(12) United States Patent
Schulman

(10) Patent No.: US 7,418,872 B2
(45) Date of Patent: Sep. 2, 2008

(54) SYSTEM AND APPARATUS FOR SENSING PRESSURE IN LIVING ORGANISMS AND INANIMATE OBJECTS

(75) Inventor: Joseph H. Schulman, Santa Clarita, CA (US)

(73) Assignee: Alfred E. Mann Foundation for Scientific Research, Santa Clarita, CA (US)

( * ) Notice: Subject to any disclaimer, the term of this patent is extended or adjusted under 35 U.S.C. 154(b) by 0 days.

(21) Appl. No.: 11/809,472

(22) Filed: Jun. 1, 2007

(65) Prior Publication Data

US 2007/0234815 A1    Oct. 11, 2007

Related U.S. Application Data

(62) Division of application No. 10/921,750, filed on Aug. 18, 2004, now Pat. No. 7,252,005.

(60) Provisional application No. 60/497,391, filed on Aug. 22, 2003.

(51) Int. Cl.
*G01L 9/00* (2006.01)
(52) U.S. Cl. ............................. 73/754; 438/50; 600/398

(58) Field of Classification Search ............... 73/700; 438/53; 600/398
See application file for complete search history.

(56) References Cited

U.S. PATENT DOCUMENTS

| 4,127,110 | A | * | 11/1978 | Bullara | ........................ 600/561 |
| 5,001,595 | A | * | 3/1991 | Dittrich et al. | ............ 361/283.4 |
| 6,030,851 | A | * | 2/2000 | Grandmont et al. | ............ 438/53 |
| 6,890,300 | B2 | * | 5/2005 | Lloyd et al. | .................. 600/398 |
| 6,939,299 | B1 | * | 9/2005 | Petersen et al. | ............. 600/398 |
| 2004/0073137 | A1 | * | 4/2004 | Lloyd et al. | .................. 600/561 |
| 2005/0268722 | A1 | * | 12/2005 | Tai et al. | ........................ 73/715 |

* cited by examiner

*Primary Examiner*—Andre J Allen
(74) *Attorney, Agent, or Firm*—Malcolm J. Romano

(57) ABSTRACT

System and apparatus for measuring pressure comprising a microelectronic device, an interface member attached to the microelectronic device, a pressure sensor having a diaphragm responsive to external pressure exerted upon the diaphragm, wherein the interface member is positioned between the microelectronic device and the pressure sensor and is attached to the pressure sensor providing a first cavity between the pressure sensor diaphragm and the interface member and wherein the pressure in the first cavity is set at an initial predetermined pressure.

21 Claims, 4 Drawing Sheets

SYSTEM AND APPARATUS FOR SENSING PRESSURE IN LIVING ORGANISMS AND INANIMATE OBJECTS

This application is a divisional of U.S. application Ser. No. 11/002,592, which claims the benefit of U.S. Provisional Application No. 60/497,391 filed on Aug. 22, 2003 and said U.S. Provisional Application No. 60/497,391 is hereby incorporated by reference herein.

DETAILED DESCRIPTION OF THE ILLUSTRATIVE EMBODIMENTS

In accordance with an exemplary embodiment, an apparatus for measuring pressure in association with a living organism or inanimate object is described. The apparatus comprises at least a microelectronic device and a pressure sensor connected thereto. In some circumstances, an interface member may be disposed between the microelectronic device and the pressure sensor. The microelectronic device can be a microstimulator and/or a microsensor. For example, a class of injectable/implantable microelectronic devices described in U.S. Pat. Nos. 5,193,539, 5,193,540, 5,312,439, 6,164,284, 6,185,452, 6,208,894, 6,315,721, 6,564,807 and incorporated by reference herein provide for stimulation of biological tissue or sensing of signals from biological tissue such as nerves or muscles as well as physiologic parameters such as body temperature. Each device includes electrical stimulation circuitry and electrodes configured in a form that is suitable for injection by means of a hypodermic needle or insertion tool. The devices can be leadless or have leads attached to them. Furthermore, each device may communicate through wireless or wired communication networks. In the case of wireless networks, microelectronic devices receive power by either inductive coupling to an externally applied electro-magnetic field or by means of an internal rechargeable battery as described in U.S. Pat. No. 6,208,894. They receive digital command signals by telemetry. The packaging and materials of the microelectronic device are selected and designed to protect its electronic circuitry from the body fluids and to avoid damage to the electrodes and the surrounding tissues from the presence and operation of the microelectronic device in those tissues. In this regard the microelectronic devices are hermetically sealed and unaffected by body fluids.

Figure 1:
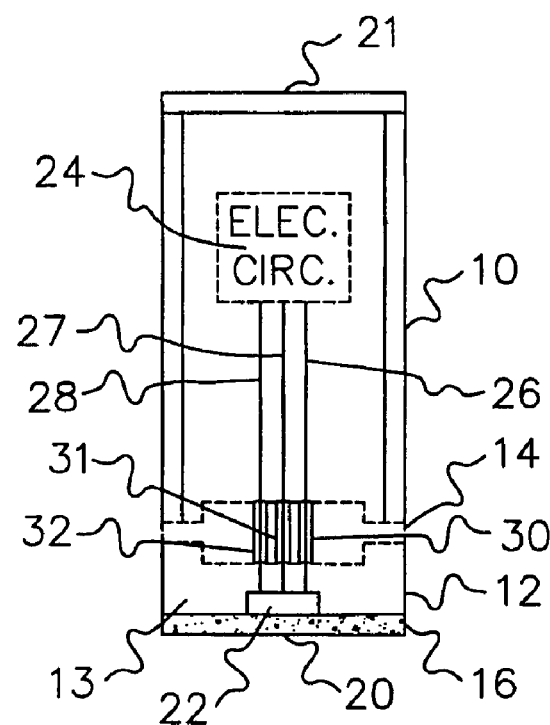
FIG. 1 is an illustration of an exemplary embodiment showing an apparatus for measuring pressure.

FIG. 1 is an illustration of an exemplary embodiment showing an apparatus for measuring pressure. A microelectronic device 10 is connected to a pressure sensor 12 allowing for measurement of pressure associated with any portions of a living organism or inanimate object or environment in the immediate proximity of pressure sensor 12. The living organism may be, among others, a human or an animal, and the inanimate object may be, for example, a vehicle tire or any other equipment that require a pressure measurement. An interface member 14 (shown in dotted lines) may be optionally disposed between the microelectronic device 10 and the pressure sensor 12. The pressure sensor 12 has a flexible portion in a form of a diaphragm 16. There is formed a hermetically sealed cavity 13 within the pressure sensor 12 and between the diaphragm 16 and the interface member 14. It is contemplated that the pressure in the hermetically sealed cavity 13 is set at an initial predetermined pressure. This initial predetermined pressure may be about one (1) atmosphere or any other desired pressure. The pressure sensor 12 may be releasably attached to the microelectronic device or the interface member, or alternatively it may be manufactured as an integrated piece with the microelectronic device or the interface member. Generally, the microelectronic device may be made of ceramic such as zirconia or alumina and the pressure sensor may be made of titanium or titanium alloy. The interface member can be made of, for example, titanium. The diaphragm 16 is responsive to the external pressure exerted thereon. For example, when the external pressure is higher than one-atmosphere, then the diaphragm 16 is pressed inward and creates a deformation which can be utilized to measure the external pressure. One of a number of techniques is to utilize a strain gauge mounted on the diaphragm 16 so that to measure the external pressure. Once the strain gauge is deformed, corresponding voltage changes produced by the gauge may be detected and calibrated as a function of pressure.

It is contemplated that the interface member 14 is connected to the microelectronic device 10 and the pressure sensor through various other attachment techniques such as brazing, soldering, welding, gluing, or other techniques known to those skilled in the relevant art. For example, when brazing the interface member 14 to microelectronic device 10, nickel or a nickel alloy may be used as the braze material. The pressure sensor is hermetically sealed through various techniques known to those skilled in the art in order to maintain a completely sealed cavity as part of the pressure sensor. To convey electrical signals from the strain gauge 22 to microelectronic device electronics 24 for processing, vias (wires) 26, 27 and 28 (and more if required) are arranged to extend through interface member hermetic feed-through 30, 31 and 32 respectively to electronics 24. To maintain hermeticity, laser welding technology may be used to seal the feed-throughs once the wires 26, 27 and 28 have been connected through the feed-throughs. It is further contemplated that the pressure sensor and the interface member may be a single-unit integrated piece.

Mere examples of pressure sensors contemplated for use in the embodiments of the invention are strain gauges, piezoelectric crystals, or any other sensors known to those skilled in the art that produce an output signal as a function of pressure or strain related mechanical disturbances to the sensor. The pressure sensor can be positioned on either the stimulating/active electrode end or the indifferent electrode end 21 of the microelectronic device. Referring to FIG. 1, when the pressure sensor 12 is positioned on the stimulating electrode end of the microelectronic device, the diaphragm of the pressure sensor can be made electrically conductive in order to maintain proper electrical conductivity for stimulation of a desired nerve or muscle. To provide adequate electrical conductivity various techniques such as sputtering may be utilized for adhering or depositing electrically conductive material 20 such as, for example, platinum, and iridium onto the surface of the pressure sensor diaphragm 16. In the alternative, a pressure sensor may be provided where its diaphragm is made of an electrically conductive material suitable for delivering electrical stimulation pulses to selected sites.

In an embodiment wherein it is desired not to have an interface member between the microelectronic device and the pressure sensor, preferably the pressure in a chamber formed by the microelectronic device and the pressure sensor should be set at the initial predetermined pressure. In order to prevent the pressure inside the chamber from changing because of the gas absorption or emission characteristic of the internal components in the microelectronic device, it is contemplated that the internal components used in the microelectronic device are made of non-gas emissive and non-gas absorbing material. The gas used in the contiguous space/chamber may be any type of inert gas such as argon. Furthermore, it is contemplated that the pressure in the contiguous space/chamber between the pressure sensor and the microelectronic device is calibrated to about one-atmosphere.

Figure 2:
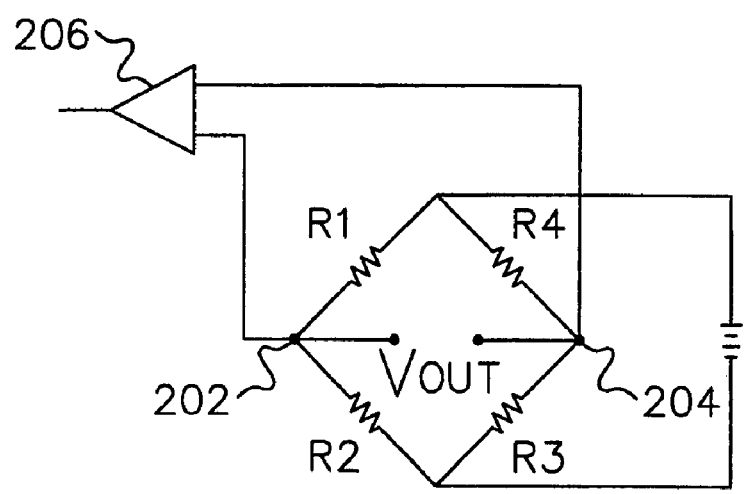
FIG. 2 is an exemplary representation of a wheatstone bridge circuit arrangement suitable for measuring pressure.

FIG. 2 is an exemplary representation of a Wheatstone Bridge circuit arrangement as part of a strain gauge suitable for measuring pressure. For example, as described above, various types of pressure sensors such as a strain gauge, among others, may be utilized with the microelectronic device. By way of illustration, under pressure changes, the strain gauge flexes such that the resistance values of R1, R2, R3, and R4 or any combination of them (depending on whether a quarter-bridge, half-bridge, or full-bridge is implemented) are changed in proportion to the sensed changing pressure condition. The change in the resistance values results in a change in the voltage value between the nodes 202 and 204. The difference in these voltages is supplied to an operational amplifier 206 which amplifies the differential signal representative of a sensed pressure. The differential signal is further provided to an analog-to-digital (A/D) converter in the microelectronic device for signal conversion and subsequent transmission to an external unit described in further detail below.

Figure 3:
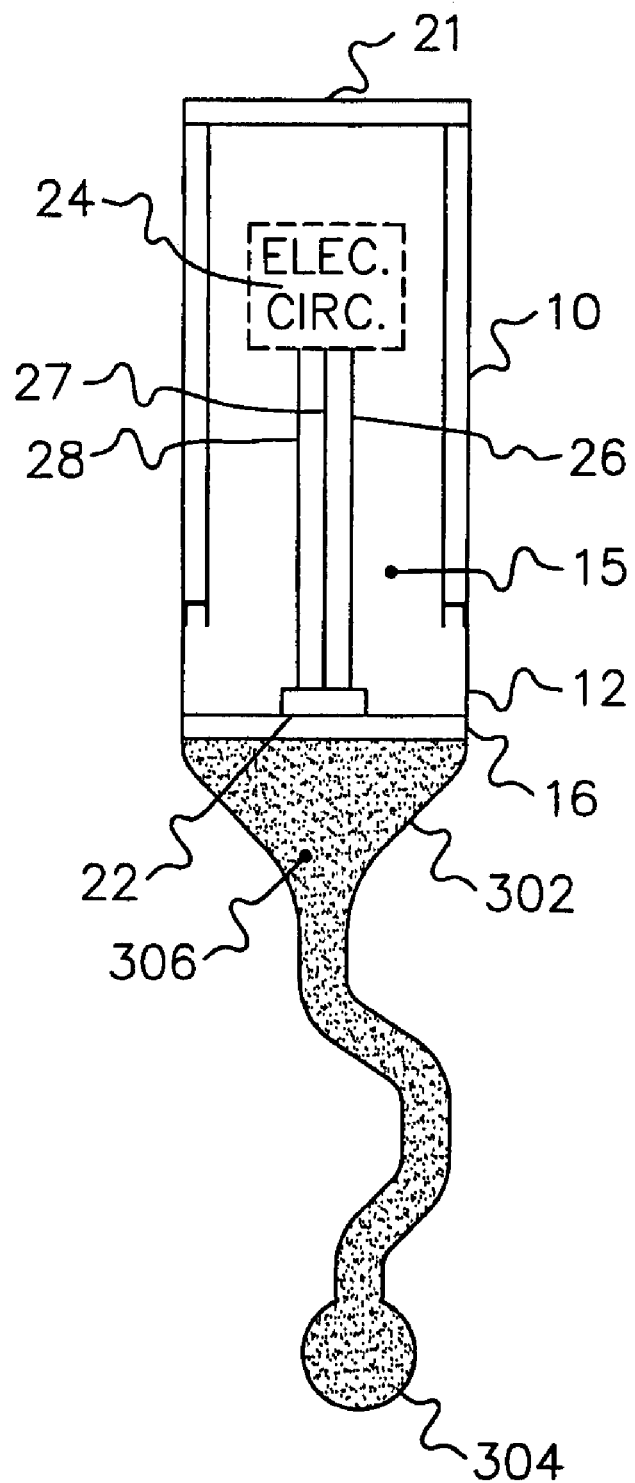
FIG. 3 is an illustration of another exemplary embodiment showing an apparatus for measuring pressure.

FIG. 3 is an illustration of another exemplary embodiment showing an apparatus for measuring pressure. In this embodiment, an elongated member 302 is attached to the pressure sensor having a squeezable distal portion 304. It is contemplated that the pressure sensor and the microelectronic device may be manufactured as an integrated piece or two separate pieces attached together. As described above, a contiguous chamber 15 is formed within the microelectronic device 10 and the pressure sensor 12, wherein the pressure therein is at the initial predetermined pressure. The elongated member comprises a body portion having a substantially non-expanding wall with incompressible fluid 306 therein which provides a medium for transferring any pressure imparted on the squeezable distal portion to the proximal end of the elongated member where it is in contact with the flexible portion/diaphragm of the pressure sensor. This embodiment provides for placement of the squeezable distal portion of the elongated member in areas of the body or an object where it is difficult to place the microelectronic device 10 with its associated pressure sensor 12. For example, the elongated member can be implanted subcutaneously near the tip of the finger of a person and the microelectronic device 10 may be placed in palm of the hand of the person. In this manner, when the distal portion is squeezed when subjected to pressure, the incompressible fluid in the elongated member is pressurized and results in a change on the diaphragm of the pressure sensor.

Figure 4:
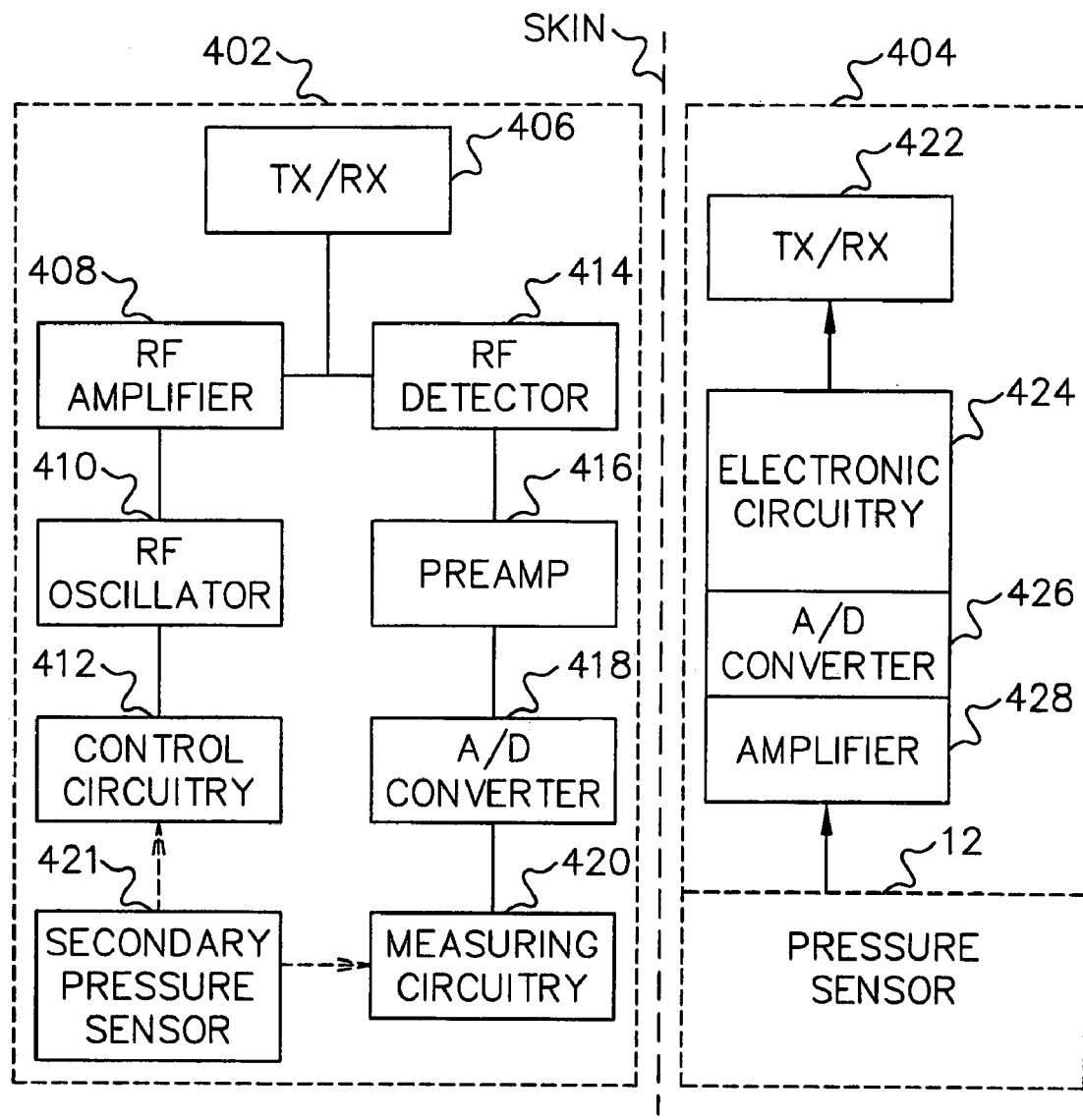
FIG. 4 is an illustration of an exemplary system utilizing the apparatus for measuring pressure.

FIG. 4 is an illustration of an exemplary system utilizing the exemplary embodiments of the apparatus described above for measuring pressure. In this system 400, an external unit 402 is provided for communication with the apparatus that may be in the form of an implantable device 404. As shown in FIG. 4, the external unit 402 broadly comprises a transmitter/receiver 406, wherein the transmitter is electrically coupled to an RF amplifier 408, RF oscillator 410, and control circuitry 412 for providing transmission of data communication containing command instructions to the implantable device 404. Although not shown, the external unit has the capability of providing power to the implantable device 404. The receiver of the external unit 402 is electrically coupled to at least an RF detector 414, a preamplifier 416, an A/D converter 418, and a measuring circuit 420 for providing a measurement of the pressure information received from the apparatus. It should be noted that the external unit 402 may also be implantable in a body. The implantable device 404 broadly comprises a transmitter/receiver 422, electronic circuitry 424, an A/D converter 426, an amplifier 428, and the pressure sensor 12. Referring to FIG. 4, in an embodiment of the system the implantable device 404 may be implanted under the skin i.e., subcutaneously, and adjacent to a desired blood vessel, lung, heart, skin pressure point, nerve or muscle for pressure sensing and/or stimulation in the body.

Figure 5:
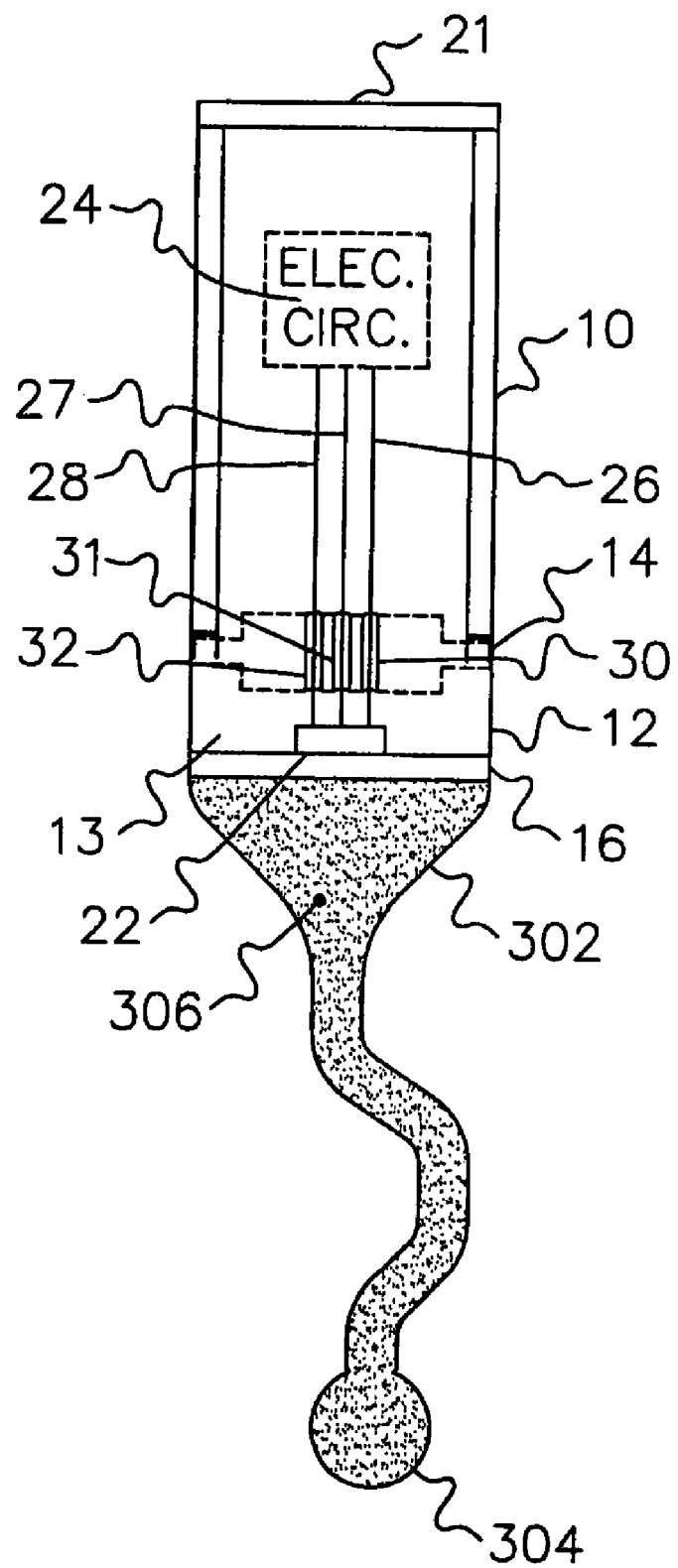
FIG. 5 is an illustration of yet another exemplary embodiment of the apparatus shown in FIG. 3.

FIG. 5 is an illustration of yet another exemplary embodiment of the apparatus shown in FIG. 3. In this embodiment, the interface member 14 is positioned between the microelectronic device 10 and the pressure sensor 12 and attached thereto. As described above, the chamber or cavity 13 is formed within the pressure sensor 12 and between the diaphragm 16 and the interface member 14. Identical to the arrangement and the operation described in connection with the exemplary embodiment shown in FIG. 3, by applying pressure to the squeezable distal portion 304 the incompressible fluid 306 transfers the change in volume to the diaphragm 16 of the pressure sensor 12 which measures the imparted pressure change. Furthermore, as described in FIG. 1, the pressure in the cavity 13 is set at an initial predetermined pressure.

It should be noted that any of the embodiments of the apparatus described herein may be implanted subcutaneously or percutaneously in a body of a living organism or placed on the surface of the body. Generally, when the apparatus is implanted subcutaneously, it utilizes wireless communication although in some circumstances it may utilize wired communication with the external unit. The dimensions of the microelectronic device are less than about 100 mm and 10 mm longitudinally (axial) and laterally respectively and preferably 60 mm and 6 mm respectively. This provides for a more efficient injection of the apparatus into the body.

In any of the embodiments described herein, the pressure sensor signal may be AC-coupled to the electronic circuitry in the microelectronic device as an example of a technique to monitor rapid pressure changes sensed by a microelectronic device but ignore very slow changes in pressure. For example, this technique is applicable for determining whether a person is walking by having the apparatus implanted in the foot of the person. In this manner, when the person sets his or her foot on the ground, the AC-coupled pressure sensor provides, for example, a voltage for charging an AC-coupled capacitor and when the person lifts his or her foot off the ground the capacitor discharges at a specific rate. If the pressure changes at a rate slower than the discharge rate, the capacitor would not be charged up. If the pressure charges at a rate faster than the discharge rate, then the voltage on the capacitor can be detected. Yet another application of the AC-coupling is for compensating for gradual changes in the atmospheric pressure surrounding the apparatus. By way of example, when the apparatus having the internal initial predetermined pressure of, for example, one (1) atmospheric pressure at sea level is displaced to a higher altitude, the diaphragm will be deformed by bulging outward to equalize the internal pressure with the surrounding pressure. As a result, the strain gauge will be deformed and will provide a voltage change that is translated into a pressure measurement. In instances where the desired pressure measurement is the pressure inside a patient's body or an inanimate object, the effects of the change in altitude could provide a potentially false measurement. The AC-coupling of the electronic circuitry in the microelectronic device to the pressure sensor compensates for the potentially false measurement by allowing relatively more rapid changes in pressure (such as stepping as described above) to be detected by the apparatus in such a way that is independent of a gradual change in pressure due to a change in altitude.

Another approach for compensating or correcting for a change in pressure due to altitude or weather systems is to provide a secondary pressure sensor means 421 (such as a barometer or another apparatus similar and consistent with the exemplary embodiments of the apparatus described herein) associated with the external unit 402 such that the secondary pressure sensor means measures the surrounding environment's atmospheric pressure. The surrounding environment's atmospheric pressure may be communicated through the external unit to the apparatus as a reference pressure. Hence, the apparatus can correctly measure a desired pressure by comparing the reference pressure with the total pressure sensed by it.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. An apparatus for measuring pressure, comprising:
   a microelectronic device;
   a pressure sensor comprising a diaphragm responsive to external pressure exerted upon the diaphragm, wherein the pressure sensor is attached to the microelectronic device, wherein a contiguous chamber is formed with the microelectronic device and the pressure sensor and wherein the pressure in the chamber is set at an initial predetermined pressure, and
   an elongated member attached and in contact with the diaphragm of the pressure sensor, wherein the elongated member comprises a body portion having a substantially non-expandable wall and a squeezable distal portion and wherein the elongated member contains incompressible fluid therein.

2. The apparatus of claim 1, wherein the microelectronic device is less than 100 mm in longitudinal dimension and less than 10 mm in lateral dimension.

3. The apparatus of claim 1, wherein the initial predetermined pressure is about 1 atmosphere.

4. The apparatus of claim 1, further comprising:
   an interface member positioned between the microelectronic device and the pressure sensor.

5. The apparatus of claim 4, wherein the microelectronic device is a microstimulator.

6. The apparatus of claim 4 wherein the microelectronic device is a microsensor.

7. The apparatus of claim 4, wherein the pressure sensor is releasably attached to the microelectronic device.

8. The apparatus of claim 1, wherein the pressure sensor is integrated with the microelectronic device.

9. The apparatus of claim 4, wherein the microelectronic device is adapted to be implanted in a living organism.

10. The apparatus of claim 4, wherein the microelectronic device is adapted for percutaneous attachment to a living organism.

11. The apparatus of claim 4, wherein the microelectronic device is adapted for subcutaneous implantation in a living organism.

12. The apparatus of claim 4, wherein the pressure sensor is hermetically sealed.

13. The apparatus of claim 1, wherein the pressure sensor is AC coupled to the microelectronic device.

14. A system for measuring pressure sensed by an implantable device, comprising:
    an implantable device, comprising:
    a microelectronic device;
    a pressure sensor having a flexible portion responsive to pressure exerted upon the flexible portion; wherein the pressure sensor is attached to the microelectronic device, wherein a contiguous chamber is formed with the microelectronic device and the pressure sensor and wherein the pressure in the chamber is set at an initial predetermined pressures;
    an external unit for communicating with the implantable device.

15. The system of claim 14, wherein the external unit and the implantable device communicate through a wireless medium.

16. The system of claim 15, wherein the external unit and the implantable device are adapted to provide data communication therebetween.

17. The system of claim 16, wherein the external unit is further adapted to provide power to the implantable device.

18. The system of claim 14, wherein the initial predetermined pressure is about 1 atmosphere.

19. The system of claim 16, wherein the external unit comprises a secondary pressure sensor means for measuring the pressure surrounding said external unit and providing thereby a reference pressure to the external unit or the implantable device for measuring the pressure sensed by the implantable device.

20. The system of claim 14, further comprising an elongated member attached and in contact with the flexible portion of the pressure sensor, wherein the elongated member comprises a body portion having a substantially non-expandable wall and a squeezable distal portion and wherein the elongated member contains incompressible fluid therein.

21. The system of claim 20, further comprising an interface member positioned between the microelectronic device and the pressure sensor providing a first cavity between the pressure sensor flexible portion and the interface member and wherein the pressure in the cavity is set at an initial predetermined pressure.

* * * * *